United States Patent
Iiyama et al.

(10) Patent No.: US 9,421,122 B2
(45) Date of Patent: Aug. 23, 2016

(54) THERMOTHERAPY AND APPARATUS FOR THERMOTHERAPY

(75) Inventors: Junichi Iiyama, Kumamoto (JP); Kazumi Kawahira, Kirishima (JP)

(73) Assignees: Kumamoto Health Science University (60%), Kumamoto (JP); Nexus Co., Ltd. (10%), Kumamoto (JP); Kagoshima University (30%), Kagoshima (JP)

( * ) Notice: Subject to any disclaimer, the term of this patent is extended or adjusted under 35 U.S.C. 154(b) by 1045 days.

(21) Appl. No.: 13/577,828

(22) PCT Filed: Feb. 7, 2011

(86) PCT No.: PCT/IB2011/000397
§ 371 (c)(1),
(2), (4) Date: Oct. 3, 2012

(87) PCT Pub. No.: WO2011/098912
PCT Pub. Date: Aug. 18, 2011

(65) Prior Publication Data
US 2013/0066407 A1    Mar. 14, 2013

Related U.S. Application Data

(60) Provisional application No. 61/302,630, filed on Feb. 9, 2010.

(51) Int. Cl.
*A61F 7/00* (2006.01)

(52) U.S. Cl.
CPC ............. *A61F 7/00* (2013.01); *A61F 2007/006* (2013.01)

(58) Field of Classification Search
None
See application file for complete search history.

(56) References Cited

U.S. PATENT DOCUMENTS

| 7,958,888 B2 * | 6/2011 | Wagner, III | A61F 7/02 128/201.28 |
| 8,539,948 B2 * | 9/2013 | Ionascu | A61F 7/007 128/201.13 |
| 2003/0131844 A1 | 7/2003 | Kumar et al. | |
| 2003/0136402 A1 | 7/2003 | Jiang et al. | |
| 2006/0212103 A1 * | 9/2006 | Wagner, III | A61F 7/02 607/108 |
| 2008/0262377 A1 | 10/2008 | Belson | |
| 2010/0294279 A1 * | 11/2010 | Ionascu | A61F 7/007 128/203.26 |
| 2012/0029408 A1 * | 2/2012 | Beaudin | A61M 1/369 604/4.01 |

FOREIGN PATENT DOCUMENTS

| JP | 2006-263425 | 10/2006 |
| WO | WO-03/047603 | 6/2003 |
| WO | WO-2006/002949 | 1/2006 |

* cited by examiner

*Primary Examiner* — Kaitlyn Smith
(74) *Attorney, Agent, or Firm* — Norris McLaughlin & Marcus, P.A.

(57) ABSTRACT

Disclosed is a thermotherapy in which a thermal gas such as hot vapor which is warm vapor is inhaled through a mouth or a nose, and the inhaled thermal gas spreads to every alveolus of lungs. Due to such a thermotherapy, the whole respiratory organ is warmed and, at the same time, heat energy is applied to blood through the alveoli of the lungs so that human body tissues are easily warmed within a short time by transferring the heat energy to whole parts of a human body by making use of the circulation of blood. Accordingly, not only a healthy person but also a patient can easily enjoy advantageous effects of a thermotherapy which is equal to or higher than advantageous effects of a sauna or hot spring.

8 Claims, 8 Drawing Sheets

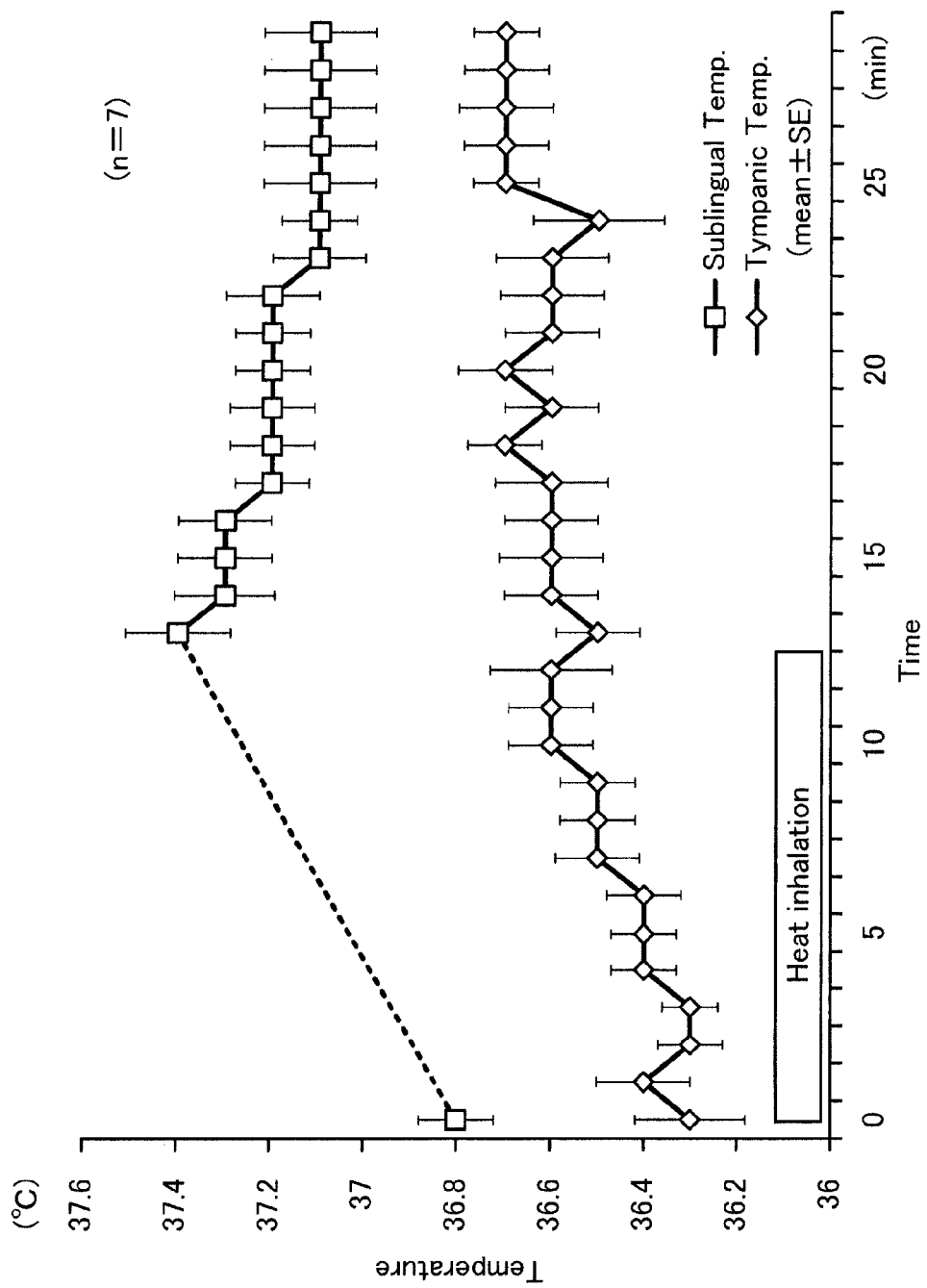

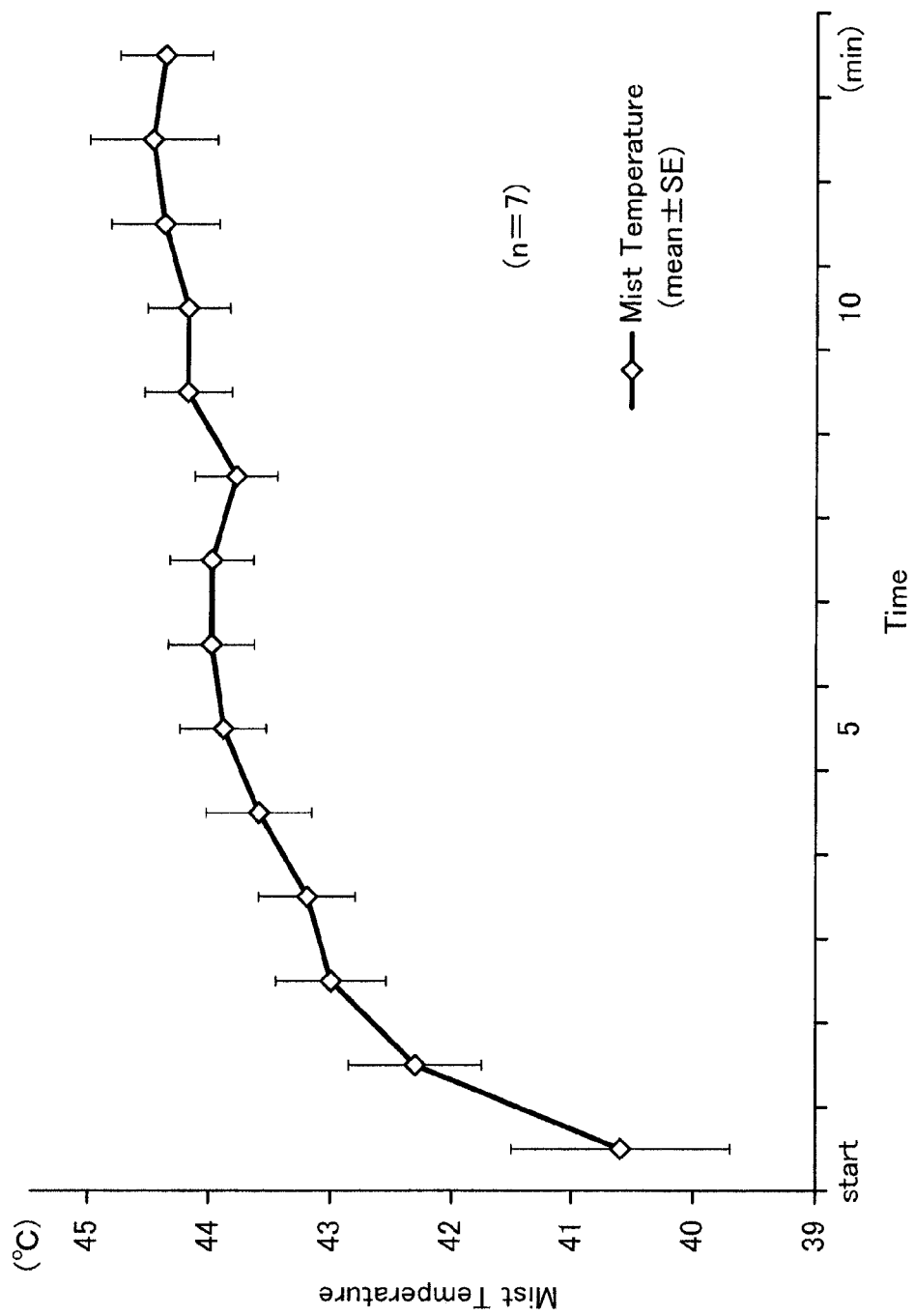

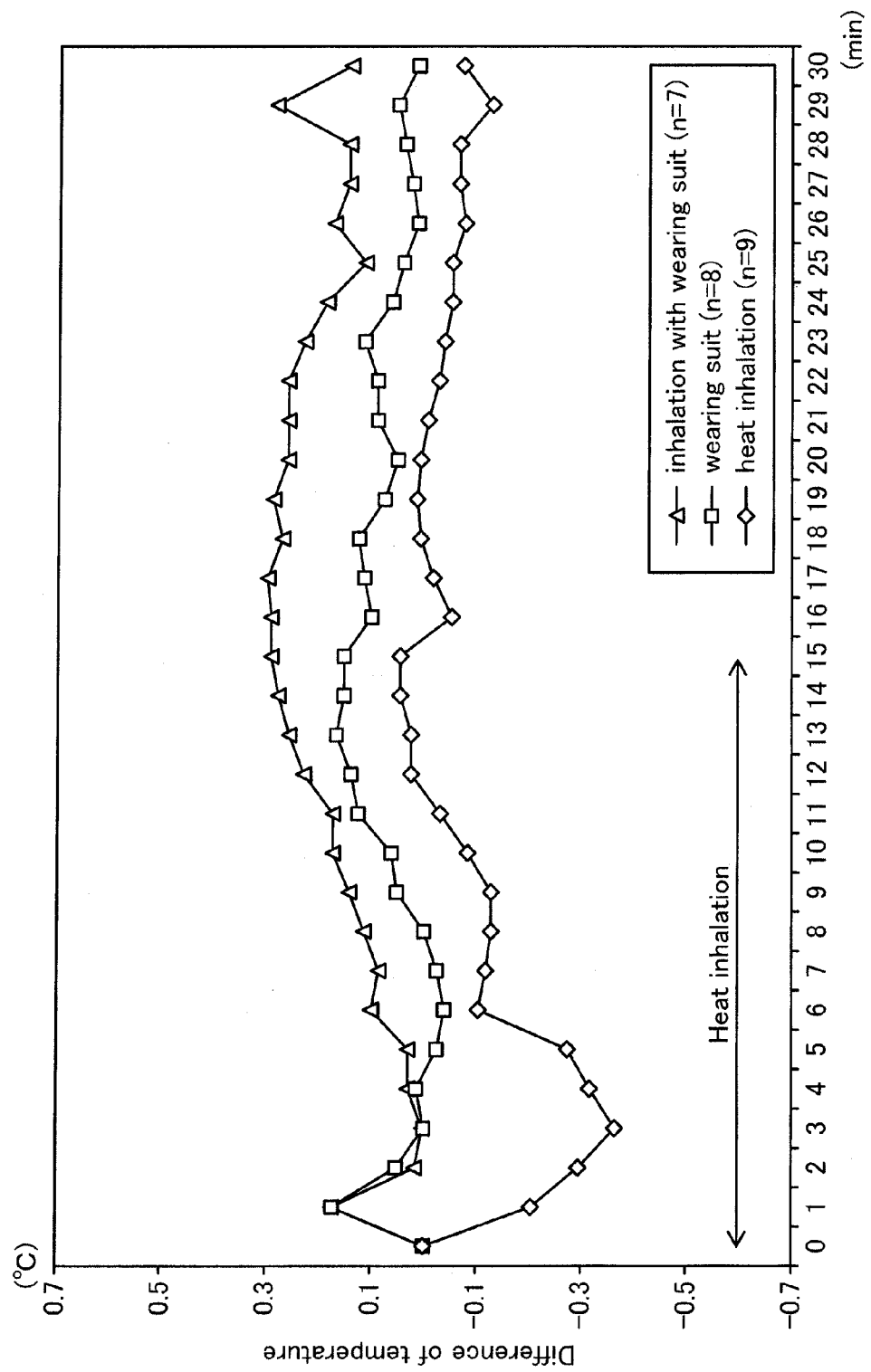

THERMOTHERAPY AND APPARATUS FOR THERMOTHERAPY

REFERENCE TO RELATED APPLICATION

Priority is claimed based on Provisional Application Ser. No. 61/302,630, filed Feb. 9, 2010.

FIELD OF THE INVENTION

The present invention relates to a thermotherapy for a human body which is performed by warming a human body through warming a respiratory organ of the human body, and an apparatus for performing the thermotherapy.

BACKGROUND OF THE INVENTION

Conventionally, as a thermotherapy, there has been known a method in which a patient warms his body by bathing in a hot spring or by taking a sauna. In such methods, blood vessels are relaxed and are widened so that the circulation of blood is enhanced. As a result, the method brings about versatile advantageous effects to the liver, kidney or heart of the patient.

However, the method warms the human body from a body surface and hence, the efficiency of warming a deep part of the human body is poor. Further, the method requires a large amount of calorific value so that a size of a warming facility becomes large thus giving rise to a drawback that it is difficult for a patient or a person who wants to use the method to easily make use of the method.

Particularly, even in a method which warms a body surface using a sauna, a portion of a thermal gas is inhaled in the respiratory organ. Accordingly, it may be considered that the principle of warming the human body from the inside has been put into practice by such a method. However, in such a method, the warming of the human body from the inside is absolutely supplementarily performed. That is, the human body is warmed mainly from the outside. In warming the human body from the body surface, the largest problem is that perspiration from a skin surface is heavy so that a heat dissipation phenomenon takes place along with the perspiration whereby the elevation of the body temperature is suppressed. Further, the concentration of the blood is increased due to the perspiration. Although some thermal gas enter alveoli of lungs through the respiratory organ, due to the increase of the concentration of the blood, the heat transfer generated by a gas exchange between the thermal gas and the blood is lowered in the alveoli of the lungs. This may be taken for granted since a sauna aims at the acceleration of the perspiration. That is, the object of using the sauna contradicts an object of the present invention that a temperature of a deep part of the human body is elevated by warming the inside of the human body. Further, in taking a sauna, the human body is warmed from the body surface and hence, the evaporation of the moisture from a skin surface is promoted so that the skin becomes dry whereby a sauna is not a therapy appropriate for patients suffering from skin diseases.

As a specific thermotherapy, for example, there has been known a technique disclosed in JP-A-2006-263425, wherein vapor containing a radon gas is evaporated by heating water in which radon ores are immersed, and a lying person inhales the evaporated vapor into his respiratory organ. This technique, however, merely aims at the elevation of a body temperature by allowing the lying person to inhale such hot vapor partially so that this technique merely has a function of elevating the body temperature in the same manner as an ordinary mist sauna. Accordingly, to elevate a temperature of a deep part of the human body by 1° C., it is necessary to humidify the human body with vapor having a temperature of 66° C. or more for 15 to 20 minutes. Although a healthy person may withstand such a thermotherapy, the application of the thermotherapy to a patient imposes a heavy physical burden on the patient. Accordingly, such thermotherapy is not applicable to the patient.

Also in this technique, in the same manner as a sauna therapy, a person may partially inhale vapor containing a radon gas into his respiratory organ. However, such a technique also mainly aims at warming a body surface. That is, a main purpose of such a technique is to promote the perspiration from the body surface so that a heat dissipation phenomenon takes place along with the perspiration whereby the elevation of the body temperature is also suppressed in this technique. That is, the object of this technique contradicts the object of the present invention that a temperature of a deep part of a human body is elevated by warming the human body from the inside.

Further, besides the above-mentioned technique, as disclosed in 2003/0136402A1, there has been known a technique in which a symptomatic therapy for the contusion of a head or the like is performed by cooling a body of a patient by allowing the patient to inhale mist through an oral cavity of the patient, wherein the mist is generated by evaporating water by making use of ultrasonic waves. Such a therapy, however, is a cooling therapy which is a therapy completely opposite to the thermotherapy. Accordingly, even when an attempt may be made to warm the cooling mist by applying a principle of the sauna to the mist, so long as the cooling therapy aims at cooling organs of a human body ranging from an oral cavity to bronchial tubes using the cooling mist, the cooling therapy cannot achieve a physiological phenomenon intrinsic to the thermotherapy, that is, the utilization of hot vapor which reaches to the alveoli of the lungs and hence, it is impossible to directly apply this cooling mist technique to the warming of the human body.

US 2003/0136402A1 also discloses a technique in which a patient inhales cooling mist and, thereafter, inhales hot mist through his oral cavity thus warming his body. However, a warming medium is mist, that is, an atomized liquid and hence, the hot mist which is inhaled through the oral cavity of the patient cannot reach alveoli of lungs. Accordingly, the hot mist cannot sufficiently brings about phenomena including the warming of blood by a gas exchange between the hot mist and blood or the heat transfer to blood in alveoli of lungs.

Further, US2008/0262377A1 discloses a technique which suggests a possibility that a patient inhales hot mist into alveoli of his lungs. However, the technique does not specifically teach a mechanism of thermotherapy through alveoli of lungs. Accordingly, in this technique, specific studies have not been made at all with respect to whether or not hot mist of a proper temperature can reach alveoli of lungs of a patient. Also specific studies have not been made at all with respect to whether or not a temperature of a deep part of a human body can be elevated by approximately 1° C. even if hot mist of a proper temperature may reach alveoli of lungs of a patient. Accordingly, there is no possibility that such a technique is actually put into practice.

That is, this technique is substantially equal to the above-mentioned technique in which the patient inhales the hot mist through his oral cavity. That is, this technique also uses mist which is an atomized liquid and hence, this technique also cannot make the hot mist reach the alveoli of the lungs. Accordingly, it is impossible to envisage a mechanism of a heat exchange between hot mist and blood in alveoli of lungs from the disclosure of US2008/0262377A1.

SUMMARY OF THE INVENTION

Accordingly, it is an object of the present invention to provide a thermotherapy which can overcome the above-mentioned drawbacks.

According to one aspect of the present invention, there is provided a thermotherapy in which a thermal gas such as hot vapor which is a warm vapor is inhaled through a mouth or a nose, and the inhaled thermal gas spreads to every alveolus of lungs. Due to such a thermotherapy, the whole respiratory organ is warmed and, at the same time, heat energy is applied to blood through the alveoli of the lungs so that human body tissues are easily warmed within a short time by transferring the heat energy to whole parts of a human body by making use of the circulation of blood. Accordingly, not only a healthy person but also a patient can easily enjoy advantageous effects of a thermotherapy which is equal to or higher than advantageous effects of a sauna or hot spring. Particularly, those patients who cannot make use of a sauna therapy can also enjoy the above-mentioned advantageous effects.

That is, the present invention allows a patient to inhale a thermal gas into alveoli of lungs of the patient through a respiratory organ thus directly warming circulating blood by a gas exchange or the heat transfer in the alveoli of the lungs. In other words, the gist of the present invention lies in a technique relating to a medical treatment, that is, a thermotherapy which can acquire remarkable medical effects by elevating a temperature of a deep part of a human body through warming of the inside of the body.

At the same time, according to the present invention, the deep part of the human body is warmed at a low temperature due to the circulation of blood and hence, a patient can obtain comfortable warmth. Accordingly, the present invention can also perform a function of imparting the mental relaxation to a person or a patient.

Particularly, the gist of the present invention lies in that the warming of the human body from the inside is performed primarily and the warming of the human body from a body surface is not performed intentionally or is performed merely secondarily. Accordingly, it is possible to repeatedly apply the thermotherapy of the present invention to patients suffering from various kinds of diseases. For example, the thermotherapy of the present invention is applicable to the cure of patients suffering from following diseases in such a manner that a temperature of a deep part of a body of the patient is elevated by 1° C. and is kept at an elevated temperature for approximately 15 minutes, and this treatment is performed once a day for approximately two or more weeks continuously.

For example, the treatment can be applied to a patient suffering from chronic arteriosclerosis, a patient suffering from burns, a patient suffering from a dialysis patient, a patient whose medicine absorption efficiency is desired to be increased. Particularly, the patient suffering from dialysis can acquire, due to the application of the thermotherapy of the present invention which warms the inside of the human body, the following advantageous effects. That is, the patient can obtain a therapeutic effect that a blood circulation state is improved so that the flow resistance in a blood vessel is decreased whereby dialysis efficiency is enhanced. Further, from a viewpoint of enhancing the medicine absorption efficiency, by applying the therapy of the present invention which warms the inside of a human body to a dialysis patient immediately before or after the patient takes medicine, it is possible to increase the absorption efficiency of a medicine which exhibits poor absorption efficiency (for example, a bisphosphonate formulation for osteoporosis) so that a medical effect can be increased. Further, by applying the therapy of the present invention in which inside of a human body is warmed to a patient suffering from intestinal malabsorption syndrome or the like, the patient can acquire an advantageous effect that the absorption of nutrients is promoted.

In this manner, by properly applying a moderate thermal burden on the alveoli of the lungs through the respiratory organ of a patient, the patient can improve a vascular endothelium function, and can enjoy an effect that arteriosclerosis which is caused by aging is slowed down. Further, heat shock protein synthesis is induced in tissues of a patient so that the present invention can also contribute to the improvement in stress tolerance and athletic ability of a person.

Thermotherapy of the present invention can also acquire another remarkable advantageous effect. That is, the thermotherapy of the present invention is performed through warming of the respiratory organ so that the thermotherapy can be performed using a simple device, requires a small calorific value, and is installable at any place whereby it is possible to perform the thermotherapy of the present invention at a low cost.

BRIEF DESCRIPTION OF THE DRAWINGS

FIG. 4 to FIG. 7 are graphs explaining data showing results of the thermotherapy according to the present invention.

DETAILED DESCRIPTION OF THE INVENTION

Figure 1:
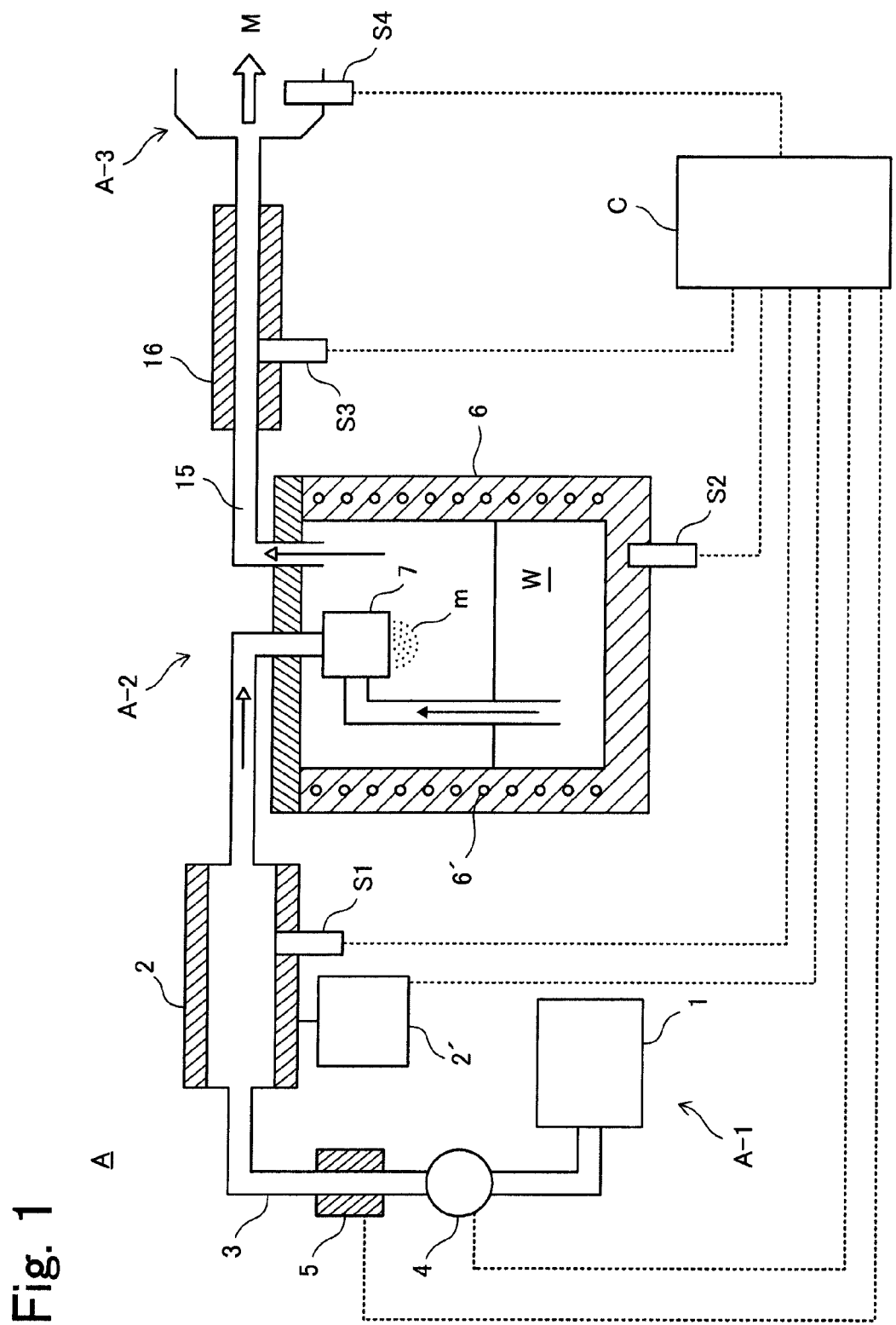
FIG. 1 is an explanatory view showing an apparatus for thermotherapy according to the present invention.

In performing the thermotherapy, the elevation of a temperature of a deep part of a human body by 1° C. has the following medical significance.

Firstly, as an immediate effect, the thermotherapy can decrease the flow resistance in all blood vessels while increasing a cardiac output and hence, it is possible to promote the circulation of blood without elevating a blood pressure. In promoting the circulation of blood, both of a preload and an after load are decreased so that a load imposed on a heart is small.

Further, it has been reported that the continuous application of the thermotherapy is effective in ameliorating arrhythmia accompanying cardiac failure, arteriosclerosis and vascular endothelium function disorders accompanying lifestyle-related disease, chronic obstructive arteriosclerosis of a lower limb, fibromyalgia disease, and physical symptoms accompanying chronic pain or mild depression, and improving an appetite. In this manner, the thermotherapy is effectively applicable to various diseases ranging from cardiac failure to arteriosclerosis, vascular disorders and physical symptoms, and it is considered that fields to which the thermotherapy is applied will be steadily increased.

Further, it has been reported that when the continuous application of thermotherapy physiologically promotes synthesis of nitrogen monoxide released from the vascular endothelium. This is the critical evidence that repeated physical stimuli caused by a heat stress modify vital functions through the gene transcription.

Accordingly, by elevating a temperature of a deep part of a human body of a healthy person by 1° C., blood vessels are relaxed and are widened so that the circulation of blood is enhanced. As a result, such elevation of the deep part of the human body brings about versatile advantageous effects to the liver, kidney or heart of the patient.

However, conventionally, as a method of elevating a temperature of a deep part of a human body, there has been solely proposed a sauna therapy or the like where a human body is warmed mainly from a body surface and mist is partially inhaled into bronchial tubes in the same manner as a mist sauna for elevating a temperature of a deep part of a human body. Particularly, hot mist used in the related art which is inhaled into the bronchial tubes has a particle size of ten and several μm or more even in an early mist forming stage and, further, the hot mist is present in the atmosphere in the vicinity of an oral cavity of a person and hence, a hot mist suction quantity is small. Further, some hot mist are adhered to cilia formed on a middle portion of bronchial tubes and is formed into a drain. Accordingly, the hot mist hardly reaches alveoli of lungs.

Further, in the conventional thermotherapy, a human body is mainly warmed from a body surface. Accordingly, in a mist sauna, it is necessary to warm a human body at a temperature of at least 60° or more for approximately 15 minutes as a heating condition.

Such a heating condition imposes a large physical burden even on a healthy person. Accordingly, such a therapy cannot be adopted for a patient at all so that it has been considered medically difficult to apply the conventional thermotherapy to the patient.

To overcome the above-mentioned problems, inventors of the present invention have made extensive studies and have developed a thermotherapy which is easily applicable to a patient without imposing a physical burden on the patient.

That is, the inventors have focused their attention on a finding that a temperature of a deep part of a human body can be elevated by 1° C. by allowing a person to inhale a hot vapor such that heat is transferred to all human body tissues through an upper respiratory tract, a lower respiratory tract and a gas exchanging organ and the like. The inventors have particularly focused their attention on a finding that a temperature of a deep part of a human body can be elevated by 1° C. by filling every alveolus of lungs which constitute a part of the gas exchanging organ with inhaled hot vapor such that heat is transferred to all human body tissues through blood capillaries distributed in the alveoli of the lungs by a gas exchange or a heat transfer.

The following is considered to be the principle of the transfer of heat to blood by a gas exchange or a heat transfer between the alveoli of the lungs and the blood.

Here, each of the alveoli of the lungs is formed of a pouch, wherein the pouch is continuously formed on a terminal portion of a branch of the respiratory organ, and has a semispherical shape. In the alveoli of the lungs, the gas exchange between air in the inside of the alveoli of the lungs and blood in blood capillaries is performed by epithelial cells which are referred to as respiratory epithelial cells.

That is, it is considered that oxygen inhaled in the alveoli of the lungs due to lung respiration associated with the respiratory movement passes through the alveoli of the lungs, and is diffused into blood in the blood capillaries in the lung. At the same time, blood is warmed due to the transfer of heat energy from hot vapor or partially-condensed mist, and the warmed blood is supplied to all human body tissues due to the circulation of the blood thus elevating a temperature of a deep part of the human body.

The total number of alveoli of right lung and alveoli of left lung is 7 to 8 hundred millions, and the total surface area becomes 100 m$^2$, that is, approximately 30 times as large as a surface area of a human body.

It is an object of the present invention to easily elevate a temperature of a deep part of the human body by 1° C. in such a manner that heat is transferred to blood in blood capillaries distributed in the alveoli of the lungs by effectively making use of a function of the alveoli of the lungs, and heat is transferred to all human body tissues due to the circulation of the blood.

In this manner, the idea of allowing a person to inhale hot vapor into alveoli of his lungs thus elevating a temperature of a deep part of his body due to a specific function of the alveoli of the lungs is an extremely novel therapy which has not been found from a conventional medical point of view, and it is an object of the present invention to provide the above-mentioned thermotherapy and an apparatus for performing the thermotherapy.

An embodiment of the present invention is explained in conjunction with drawings.

Hereinafter, an apparatus for thermotherapy is explained in conjunction with FIG. 1 and FIG. 2.

As shown in FIG. 1, the apparatus A is constituted of a heated-air generation part A-1, a vapor generation part A-2 and a blow-off (jet) nozzle part A-3.

In the heated-air generation part A-1, a pressurized gas generated by a compressor flows into a gas flow passage 3, and is heated at a temperature of approximately 40 to 45° C. by a heating device arranged in the midst of the gas flow passage 3.

Numeral 4 indicates a speed control part which is arranged in the midst of the gas flow passage 3 and upstream of the heating device 2. The speed control part 4 adjusts a flow speed of the gas thus adjusting humidity of vapor generated by the vapor generation part A-2 described later. In the drawing, numeral 2' indicates a temperature controller in the heating device 2.

Numeral 5 indicates a flow rate sensor which is arranged in the midst of the gas flow passage 3 between the speed control part 4 and the heating device 2.

A terminal end of the gas flow passage 3 is communicably connected with the vapor generation part A-2.

That is, in the vapor generation part A-2, water W is reserved in a hermetically-sealed heat insulation casing 6. A vapor generator 7 is arranged in the heat insulation casing 6 above reserved water W. The vapor generator 7 is communicably connected with the terminal end of the gas flow passage 3.

Figure 2:
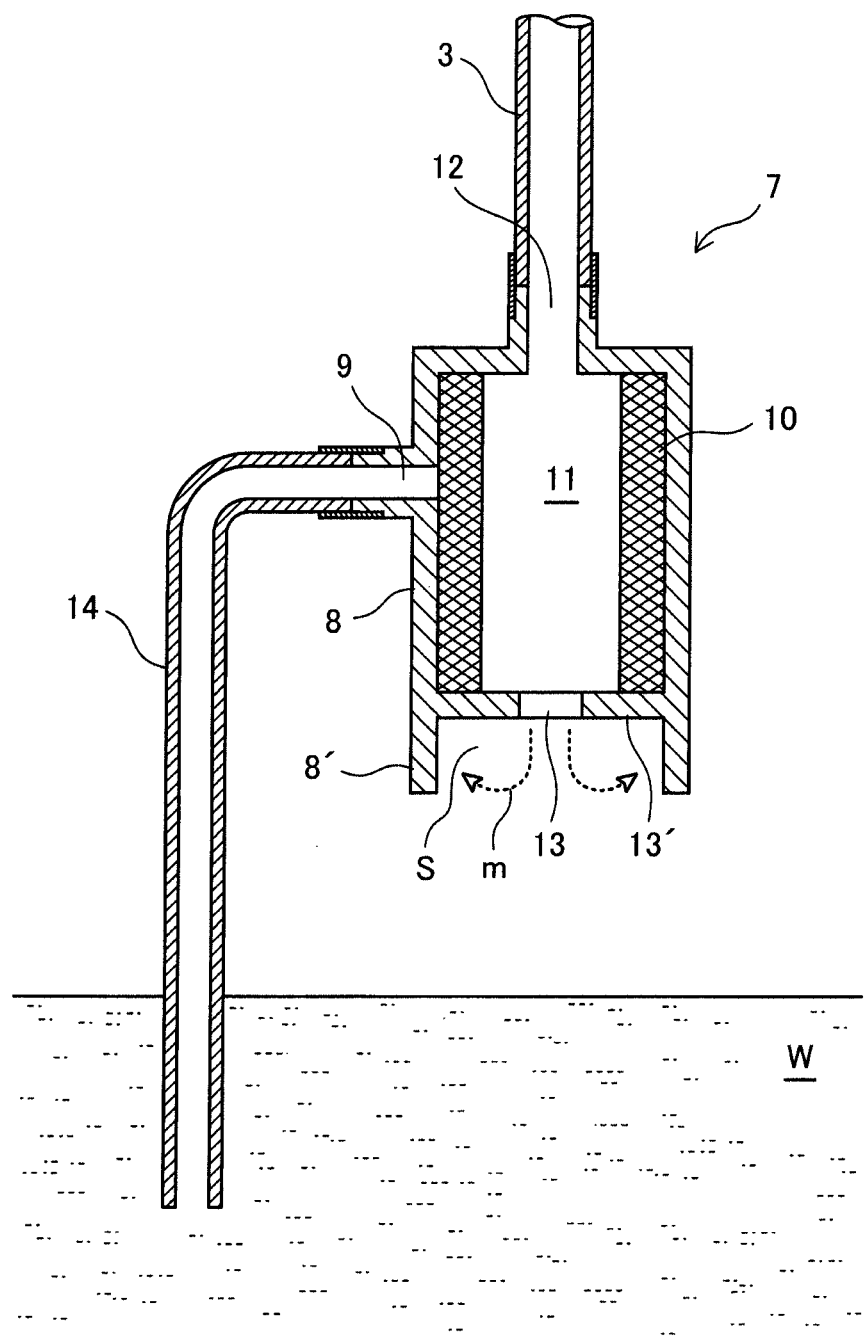
FIG. 2 is a view for explaining a cross section of a vapor generator in a vapor generation part of an apparatus for performing the thermotherapy according to the present invention.

As shown in FIG. 2, the vapor generator 7 includes a vapor casing 8 which has a box shape, and a predetermined number of water supply ports 9 are formed in a peripheral wall of the vapor casing 8. A cylindrical filter 10 formed of a nonwoven fabric is mounted on an inner peripheral wall of the vapor casing 8.

Upper ends of water supply pipes 14 are communicably connected with the water supply ports 9 of the vapor generator 7, and lower ends of the water supply pipes 14 are immersed into reserved water W and open in the reserved water W.

A flow passage 11 is formed in the inside of the cylindrical filter 10, wherein a start end of the flow passage 11 constitutes an inlet 12, and a terminal end of the flow passage 11 constitutes a blow-off outlet 13.

The terminal end of the gas flow passage 3 is communicably connected with the inlet 12 of the filter 10.

Due to such a constitution, a gas which is heated at a predetermined temperature by the heating device 2 flows into the flow passage 11 through the gas flow passage 3 at a predetermined pressure and, then, the gas is blown off from the blow-off outlet 13 which is formed in a bottom plate 13' of the vapor casing 8 and has a small diameter. Due to an injection effect generated in the flow passage 11, the reserved water W is sucked into the flow passage through the water supply pipes 14 by way of the filter 10. Here, the water W passes through meshed interstices or pores formed in the filter 10 formed of the nonwoven fabric so that the water W is atomized thus forming a mist or a mist moisture.

In this manner, a hot vapor m which is formed of the heated gas supplied through the gas flow passage 3 and atomized moisture supplied through the water supply pipe 14 by way of the filter 10 is discharged through the blow-off outlet 13 of the flow passage 11, and the hot vapor m is filled in a space defined above the reserved water W in the hermetically-sealed heat insulation casing 6.

Here, a lower end of the vapor casing 8 extends from the bottom plate 13' thus forming a skirt portion 8'. Accordingly, when the hot vapor m is blown off to the outside in a diffused state due to an orifice function of the blow-off outlet 13 formed in the bottom plate 13', the hot vapor m is agitated in a space portion S defined by the skirt portion 8' of the vapor casing 8 so that some mist particles are crushed and are vaporized. The vaporized mist particles form the hot vapor m, and the hot vapor m is filled in the hermetically-sealed heat insulation casing 6.

To prevent the hot vapor m which is blown off through the blow-off outlet 13 and is filled in the hermetically-sealed heat insulation casing 6 from turning into a drain and to keep the hot vapor m at the same temperature as the heated gas supplied through the gas flow passage, a heat retaining heater 6' is embedded in a wall of the hermetically-sealed heat insulation casing 6.

The hot vapor m filled in the hermetically-sealed heat insulation casing 6 increases the inner pressure in the hermetically-sealed heat insulation casing 6 so that the hot vapor m is introduced into a vapor pipe 15 whose start end is communicably connected with a discharge outlet formed in a ceiling portion of the hermetically-sealed heat insulation casing 6.

The blow-off nozzle part A-3 having a shape of a mask is communicably connected with a terminal end of the vapor pipe 15.

For preventing the hot vapor m from being cooled thus being formed into a drain, a heat retaining heater 16 is mounted on an outer periphery of a middle portion of the vapor pipe 15.

Due to such a constitution, the hot vapor m conveyed through the vapor pipe 15 is blown off from the blow-off nozzle part A-3 at a predetermined pressure.

By blowing off the hot vapor m into an oral cavity M in a state that the oral cavity M is covered with the blow-off nozzle part A-3 having a mask shape, the hot vapor m reaches lungs of a patient by way of a respiratory organ and, then, reaches alveoli of the lungs. Here, it is sufficient that the blow-off nozzle part A-3 has a shape which allows the hot vapor m into the oral cavity so that, for example, the blow-off nozzle part A-3 may have a shape which allow a patient to hold the blow-off nozzle part A-3 in his mouth.

Symbol C indicates a control part. The control part C performs a control of the speed control part 4, the heating device 2, the heat retaining heaters 6, 16 and the like for blowing off optimum hot vapor m based on data detected by sensors S1, S2, S3, S4 which are arranged on the heating device 2 of the heated-air generation part A-1, the hermetically-sealed heat insulation casing 6, the heat retaining heater 16 and the blow-off nozzle part A-3 respectively, data from the flow rate sensor 5 and the like.

Due to a coupled effect of a gas exchange between the hot vapor m which reaches the alveoli of the lungs and contains oxygen and blood in blood capillaries distributed in walls of the alveoli of the lungs and the heat transfer from the heated hot vapor m to the blood, heat is transferred to all human body tissues due to the circulation of the blood.

That is, the gas exchange, the heat transfer and the like are performed between the hot vapor m and blood in the alveoli of the lungs thus circulating warmed blood through all human body tissues. Accordingly, compared to a conventional technique which elevates a temperature of a deep part of a human body by 1° C. by warming the human body at high temperature mainly from a body surface, the thermotherapy of the present invention can simply and easily elevate a temperature of the deep part of the human body while reducing a burden imposed on the body as much as possible thus realizing the application of the thermotherapy to the patient.

The blow-off nozzle part A-3 is not always necessary to be formed of a nozzle having the structure which blows off vapor, and it is sufficient for the blow-off nozzle part A-3 to have the structure which functions as a heat applying device. For example, the blow-off nozzle part A-3 may have the following structure. The blow-off nozzle part A-3 is formed into a helmet-shaped bowl which can surround a head of a patient and supplies hot vapor or heated saturated-steam which is a heated gas into an respiratory tract through his oral cavity so that heat is applied to his respiratory tract.

Here, an amount of air inhaled by an average adult per one respiration is approximately 400 to 500 cc, and the number of respirations per minute is approximately 12. That is, the average adult can inhale the above-mentioned hot vapor of approximately 4.8 to 6.0 L per minute. Here, the apparatus for thermotherapy of the present invention can generate hot vapor of at least 30 L per minute and hence, the apparatus for thermotherapy of the present invention can supply an amount of hot vapor sufficient for elevating a body temperature of a patient to the inside of the patient with normal respiration of hot vapor.

Figure 3A:
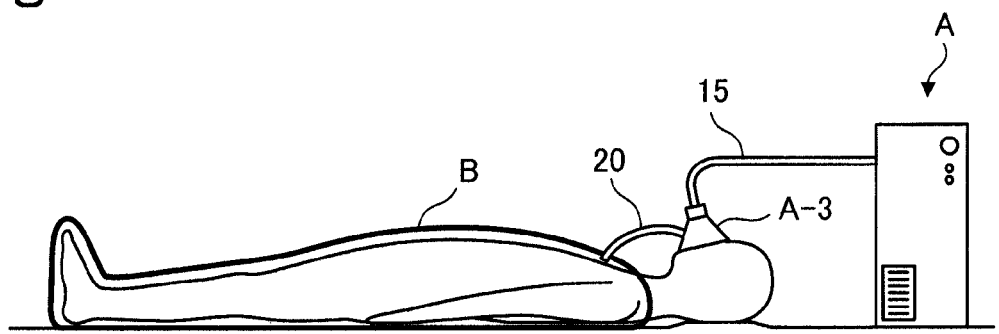
FIG. 3A to FIG. 3C are explanatory views showing embodiments for performing the thermotherapy according to the present invention.
Figure 3B:
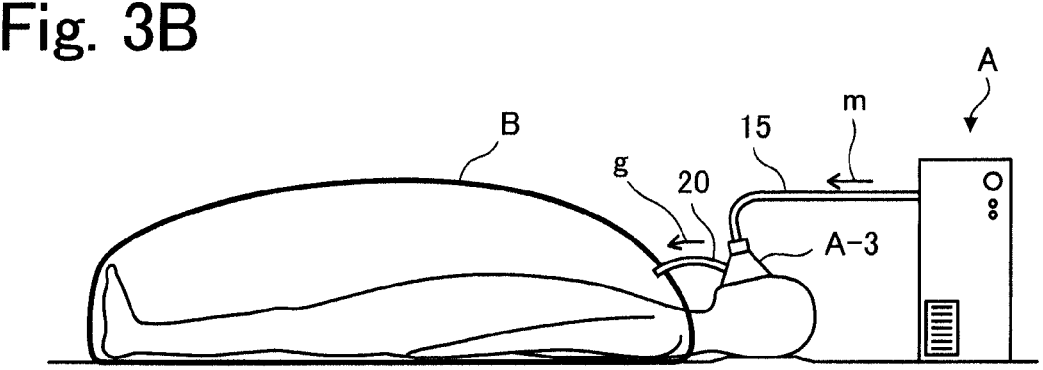
Figure 3C:
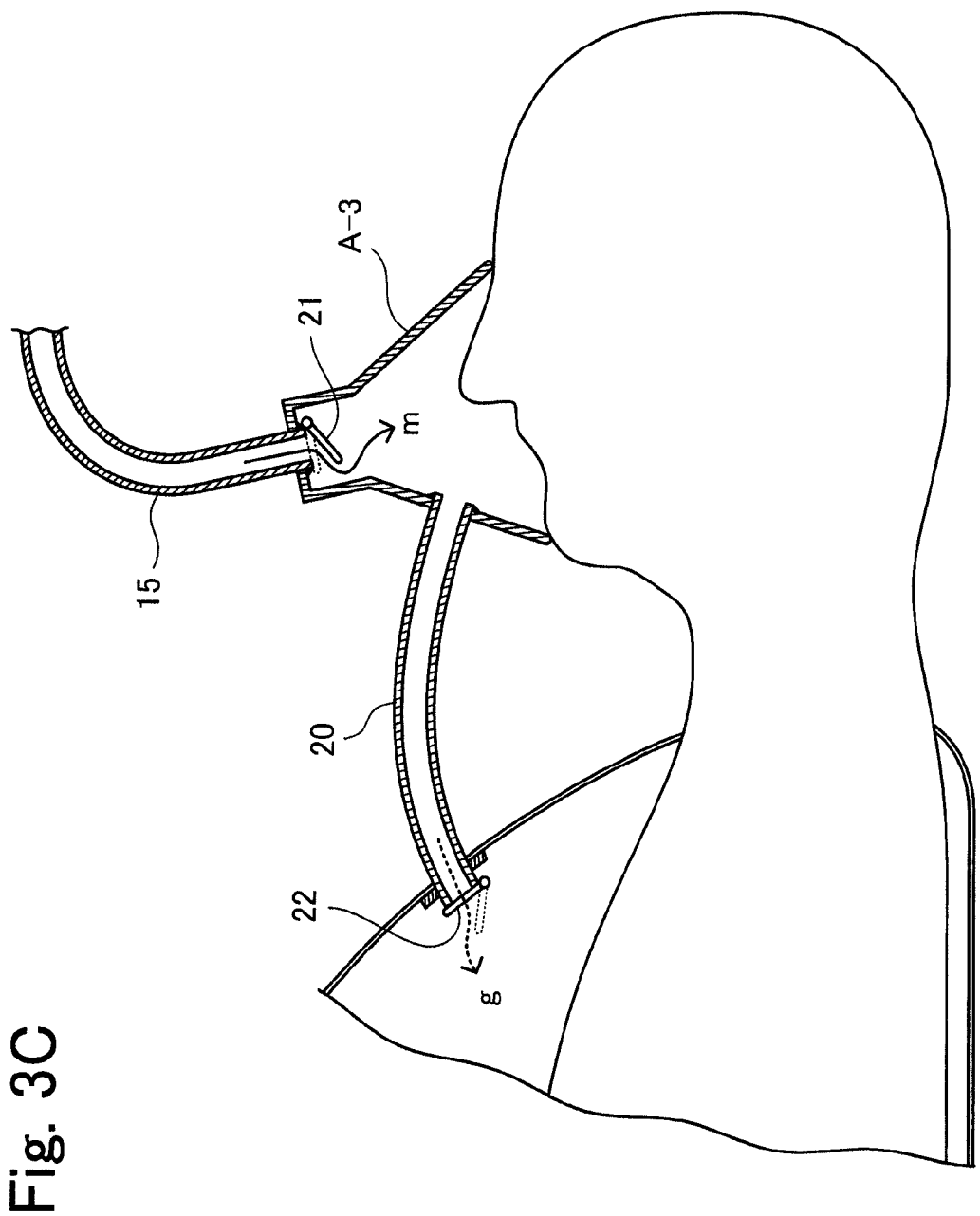

One embodiment of a mode for carrying out the thermotherapy of the present invention is explained in conjunction with FIG. 3A to FIG. 3C.

Here, FIG. 3A shows a state of the apparatus for thermotherapy before a patient inhales hot vapor m. FIG. 3B shows a state of the apparatus for thermotherapy during or after the patient inhales the hot vapor. FIG. 3C shows the blow-off nozzle part A-3 and an area around the connection part of the heat insulation suit B and a discharge pipe 20 in an enlarged manner. FIG. 3C also shows positions of a one-way check valve 21 and a one-way check valve 22 which are operated when a patient inhales the hot vapor m. The heat retaining heater 16 and the control part C are not shown in these drawings.

As shown in FIG. 3A to FIG. 3C, the apparatus of this embodiment is provided with a heat insulation suit B for covering a human body.

That is, the heat insulation suit B is made of a flexible material and is formed into a shape and with a size which can wholly cover a human body from a neck to a toe, and a naked patient wears the heat insulation suit in advance such that his neck and his head are put outside the heat insulation suit. The inside of the heat insulation suit is hermetically sealed in a state where the suit wholly covers the patient from his neck to toe so that the heat insulation suit B prevents the radiation of heat from a body surface of the patient whereby the body temperature is maintained.

Further, a flexible discharge pipe 20 is communicably connected to a predetermined portion of the heat insulation suit B, and a start end of the discharge pipe 20 is communicably connected to the inside of the blow-off nozzle part A-3.

Due to such a constitution, a discharged gas g which is discharged into the inside of the blow-off nozzle part A-3 from an oral cavity of the patient is stored in the inside of the heat insulation suit B by way of the discharge pipe 20 so that heat of the discharged gas g which is discharged by the patient also warms the body surface of the patient. Due to such a constitution, both the hot vapor inhaled into the alveoli of the lungs and the discharged gas g are utilized for elevating a body temperature as much as possible in a cooperative manner.

Here, provided that the heat insulation suit B is made of a material which is stretchable and flexible and hardly releases heat to the outside, any heat insulation suit can be used as the heat insulation suit B. Further, the heat insulation suit B is made of a material which allows the heat insulation suit B to bulge with the supply of the discharged gas g discharged from the patient.

Further, as shown in FIG. 3C, the one-way check valve 21 which opens only in the blow-off direction is provided to a terminal end of the vapor pipe 15 which is connected to the blow-off nozzle part A-3. Accordingly, it is possible to prevent the backflow of the discharged gas g discharged by the patient to the vapor pipe 15 from the inside of the blow-off nozzle part A-3 having a mask shape. Further, the one-way check valve 22 which opens only in the discharge direction is provided to a terminal end of the discharge pipe 20 which is communicably connected with the heat insulation suit B thus preventing the backflow of the discharged gas g which is discharged into the heat insulation suit B to the inside of the blow-off nozzle part A-3.

The check valve 21 and the check valve 22 move to positions indicated by a dotted line respectively when the patient discharges the discharge gas g. It is sufficient that the check valve 21 and the check valve 22 have the structure which can prevent the backflow of the discharge gas g so that the structure of the check valve 21 and the check valve 22 is not limited to the illustrated one. Further, also with respect to a connection part which connects the discharge pipe 20 to the blow-off nozzle part A-3 and a connection part which connects the discharge pipe 20 to the heat insulation suit B, it is sufficient that these connection parts allow the supply of the discharge gas g into the inside of the heat insulation suit B as described above.

Due to such a constitution, when hot vapor m is blown off into an oral cavity M in a state where a patient wears the heat insulation suit B and the blow-off nozzle part A-3 of the apparatus A for performing the thermotherapy is arranged at a position close to the oral cavity M, the hot vapor m reaches lungs by way of a respiratory organ and, then, reaches alveoli of the lungs. At the same time, the discharged gas g which is discharged into the inside of the blow-off nozzle part A-3 through the oral cavity of the patient is stored in the inside of the heat insulation suit B by way of the discharge pipe 20 so that heat of the discharged gas g also warms the body surface of the patient. Due to such a constitution, both the hot vapor inhaled into the alveoli of the lungs and the discharged gas g are utilized for elevating a body temperature as much as possible in a cooperative manner.

In this manner, when the hot vapor m is inhaled into the human body by way of the vapor pipe 15, the heat exchange is performed between the hot vapor m and blood in blood capillaries distributed in an upper respiratory tract, a lower respiratory tract and a gas exchanging organ, and the hot vapor m is discharged to the outside of the human body as the discharge gas g. At the same time, the discharge gas g having a predetermined temperature is discharged into and stored in the inside of the heat insulation suit B by way of the discharge pipe 20 so that heat of the discharged gas g warms the body surface of the patient.

The effect obtained by performing the thermotherapy of the present invention in which the human body is warmed through warming the respiratory organ is verified as follows. FIG. 4, FIG. 5, FIG. 6 and FIG. 7 are explanatory data graphs showing a result obtained by performing the thermotherapy of the present invention.

FIG. 4 is a graph showing a change with time in a sublingual temperature and a tympanic temperature.

Figure 5:
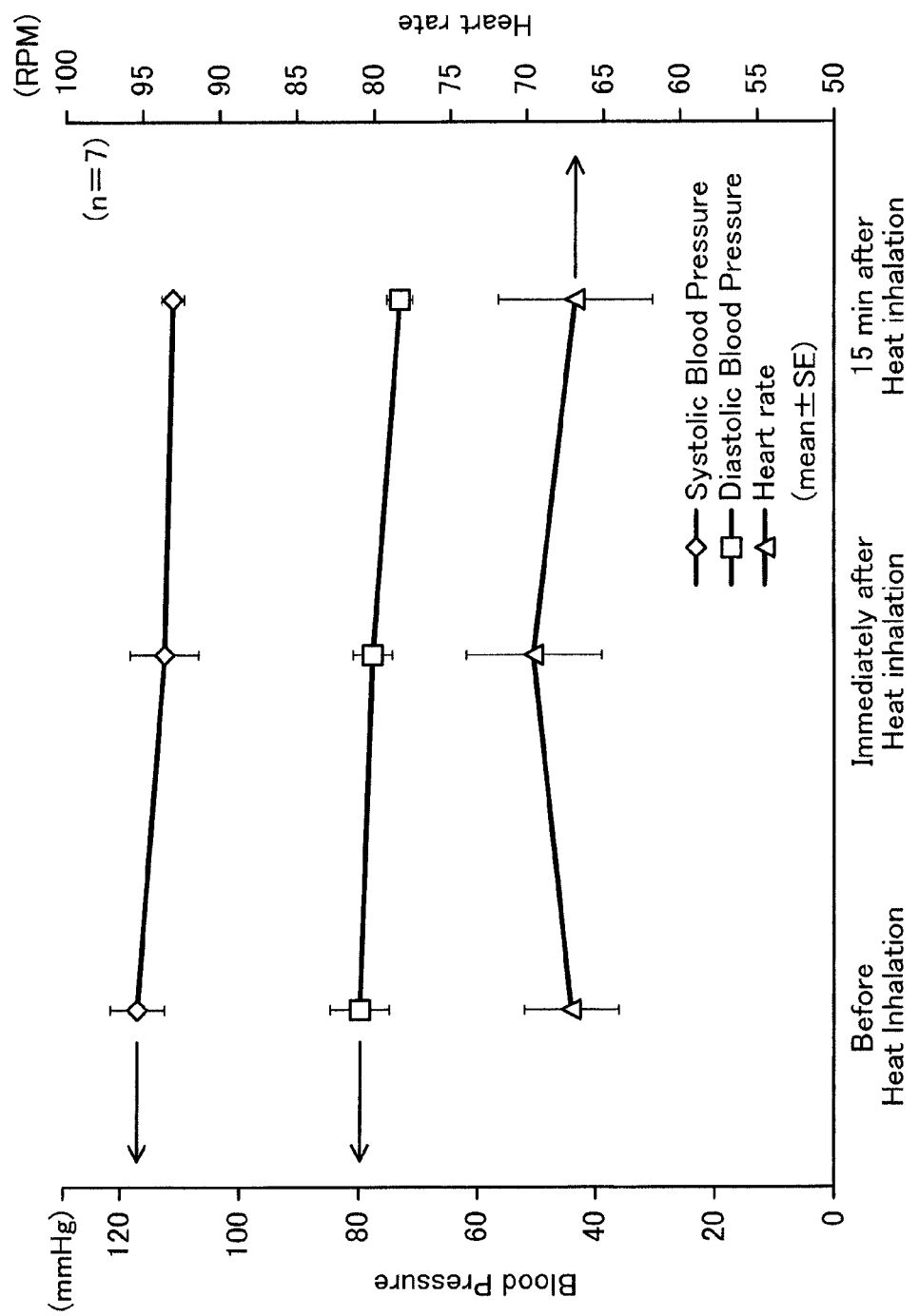

FIG. 5 is a graph showing a change with time in a blood pressure and a heart rate.

FIG. 6 is a graph showing a change with time in a temperature of the hot vapor.

FIG. 7 is a graph showing a change with time in a tympanic temperature in a case where only the apparatus for thermotherapy of the present invention is used, a change with time in a tympanic temperature in a case where the apparatus for thermotherapy of the present invention is used in a state where the human body is covered with the heat insulation suit, and a change with time in a tympanic temperature in a case where the human body is only covered with the heat insulation suit.

Firstly, the inhalation of the warm vapor is conducted on a healthy male for 12 minutes using the apparatus A of the present invention. Here, the subject is covered with a heat insulation suit for preventing the radiation of heat from the body surface, and a sublingual temperature, a tympanic temperature, a blood pressure and a heart rate of a healthy male are measured. The result is such that, as shown in FIG. 4, the sublingual temperature immediately after completion of the 12-minute warming through warming the respiratory organ is elevated from (36.8±0.09) degrees Celsius to (37.4±0.16) degrees Celsius.

The tympanic temperature is elevated from $(36.3\pm0.12)°$ C. to $(36.5\pm0.09)°$ C.

Further, as shown in FIG. 5, the blood pressure is decreased from (117.1±4.64) mmHg to (112.5±5.75) mmHg in a systolic phase and from (79.8±4.75) mmHg to (77.8±3.22) mmHg in a diastolic phase.

The heart rate is increased from (67.0±3.04) beats per minute to (69.5±4.39) beats per minute.

Thereafter, the sublingual temperature, however, is decreased to $(37.1\pm0.12)°$ C., the tympanic temperature is elevated to $(36.8\pm0.05)°$ C., the blood pressure is decreased to (111.4±1.72) mmHg in the systolic phase and (73.4±2.27) mmHg in the diastolic phase, and the heart rate is decreased to (66.8±5.03) beats per minute.

In this manner, the body temperature, the blood pressure, and the heart rate are changed after the subject inhales the warm vapor for 12 minutes. That is, as a result of inhaling the warm vapor (start of the thermotherapy), the tympanic temperature is increased at a more moderate rate than the sublingual temperature and, thereafter, although the sublingual temperature gradually falls, the tympanic temperature continues to rise. It is considered that this change results from the fact that the heat supplied to the respiratory tract is transferred to the whole body through the bloodstream.

Further, as shown in FIG. 7, in the case where the subject inhales the hot vapor using the apparatus for thermotherapy of the present invention in a state where the human body is covered with the heat insulation suit, it is found that a temperature of the whole body is kept at a higher temperature for a long time. Accordingly, it is considered that the apparatus for thermotherapy of the present invention can be used more effectively under the condition that the human body is covered with the heat insulation suit so that the radiation of heat from the body surface is prevented.

One of the reasons that the apparatus for thermotherapy of the present invention can acquire the effects shown in graphs of FIG. 4 to FIG. 7 lies in that the alveoli of the lungs have a total surface area approximately 30 times as large as a total surface area of a human body so that the warming through the respiratory organ promotes the elevation of a temperature of a deep part of the human body whereby the warming through the respiratory organ is the most effective way in warming the whole body.

Although the embodiment of the present invention has the constitution described above, any specific technique may be adopted provided that the technique can perform the whole-body thermotherapy in which the human body is warmed through warming the respiratory organ basically.

For example, with respect to the apparatus for thermotherapy, it is also possible to perform a temperature control in the heated-air generation part A-1 which constitutes a heat source. Due to such a temperature control, a temperature of the deep part of the human body can be elevated by an amount substantially equal to an amount of the temperature elevation resulting from a low-temperature sauna.

In this regard, when the vapor gas to be inhaled contains nutritive substances or medicinal properties therein, it is also considered that the nutritive substances or medicinal properties are absorbed into blood in addition to the warming effect through the respiratory organ so that various therapeutic effects can be obtained.

Furthermore, with respect to a blow-off mode of vapor, by adjusting a blow-off pressure or by changing a blow-off shape of vapor, the distribution efficiency of vapor through the respiratory tract from the mouth cavity to the alveoli of the lungs can be improved.

Although the present invention is intended to provide the novel thermotherapy which has not existed conventionally, in particular, the thermotherapy in which the human body is warmed through warming blood which circulates through the alveoli of the lungs of the respiratory organ, the present invention is also intended to provide the apparatus which can perform the warming through the respiratory organ anywhere with a simple operation.

By providing such an apparatus with a simple constitution, the thermotherapy through the respiratory organ can be easily performed to a patient who is ill in bed at home or in a hospital in need of nursing care.

Therefore, the apparatus for thermotherapy according to the present invention is required to be structurally compact. Also, it is necessary for the apparatus to be manufactured at a low cost and to have an easily portable size and structure.

The thermotherapy according to the present invention performs warming the alveoli of the lungs of the respiratory organ and hence, the thermotherapy can achieve the object of the present invention with a small amount of heat.

Since the apparatus is only required to have the structure for blowing off vapor which requires a small amount of calorific value, it is possible to easily form the apparatus in a compact shape.

What is claimed is:

1. A thermal therapy applied to a human body, comprising: elevating a temperature of a deep part of a human body by 1° C. and maintaining said elevated temperature for at least 15 minutes, said elevating and maintaining being achieved by allowing a person to inhale hot vapor such that heat is transferred to blood in capillary vessels distributed through an upper respiratory tract, a lower respiratory tract and a gas exchanging organ; and
wherein said elevating and maintaining is performed at least once per day for at least two weeks.

2. The thermal therapy applied to a human body according to claim 1, wherein the gas exchanging organ is lungs of the human body, and gas exchange occurs at alveoli of the lungs.

3. The thermal therapy applied to a human body according to claim 1, further comprising:
covering a surface of the human body with a heat insulation material during said elevating the temperature of the deep part of the human body.

4. An apparatus for elevating a temperature of a deep part of a human body comprising:
a heated air generating part;
a vapor generating part which is communicably connected with the heated air generating part;
a blow-off nozzle part which is communicably connected with the vapor generating part; and
a heat insulation suit which covers said human body; and
wherein the vapor generating part and the blow-off nozzle part are communicably connected with each other by way of a one-way check valve which opens only in a blow-off direction; and
wherein a mist or a mist moisture generated by the vapor generating part is made from reserved water in a hermetically-sealed heat insulation casing and is brought into contact with a heated gas heated by the heated air generating part so that the hermetically-sealed heat insulation casing is filled with a hot vapor, and the hot vapor in the hermetically-sealed heat insulation casing is blown off from the blow-off nozzle part at a predetermined pressure through a vapor pipe and the vapor pipe is heated by a heat retaining heater, whereby the hot vapor is introduced into alveoli of lungs through an oral cavity.

5. The apparatus for thermal therapy according to claim 4, wherein the heat insulation suit and the blow-off nozzle part are communicably connected with each other by way of a one-way check valve which opens only in the discharge direction so as to store a discharged gas discharged from an oral cavity in the heat insulation suit.

6. An apparatus for thermal therapy applied to a human body comprising:
a heated air generating part;
a vapor generating part which is communicably connected with the heated air generating part;
a blow-off nozzle part which is communicably connected with the vapor generating part; and
a heat insulation suit which covers a human body; and
wherein the vapor generating part and the blow-off nozzle part are communicably connected with each other by way of a one-way check valve which opens only in a blow-off direction, and a heated gas generated by the heated air generating part and a mist moisture generated by the vapor generating part are mixed with each other thus forming a hot vapor, and the hot vapor is transferred to the blow-off nozzle part and is introduced into alveoli of lungs through an oral cavity;

wherein the vapor generating part comprises: a hermetically-sealed heat insulation casing; and a vapor generator which is arranged in the heat insulation casing above reserved water and is communicably connected with the heated air generating part;

wherein the vapor generator comprises: a vapor casing which has a box shape, and has a predetermined number of water supply ports formed in a peripheral wall thereof; and a cylindrical filter formed of a nonwoven fabric which is mounted on an inner peripheral wall of the vapor casing;

wherein a water supply pipe is communicably connected with the water supply ports, and a lower end of the water supply pipe is immersed into the reserved water; and wherein a flow passage is formed in the inside of the cylindrical filter, wherein a start end of the flow passage is communicably connected with the heated air generating part, and a terminal end of the flow passage constitutes a blow-off outlet for the hot vapor.

7. The apparatus for thermal therapy according to claim 4, wherein the vapor generating part: comprises the hermetically-sealed heat insulation casing; and a vapor generator which is arranged in the heat insulation casing above reserved water and is communicably connected with the heated air generating part, the vapor generator comprises: a vapor casing which has a box shape, and has a predetermined number of water supply ports formed in a peripheral wall thereof; and a cylindrical filter formed of a nonwoven fabric which is mounted on an inner peripheral wall of the vapor casing, a water supply pipe is communicably connected with the water supply ports, and a lower end of the water supply pipe is immersed into the reserved water, and a flow passage is formed in the inside of the cylindrical filter, wherein a start end of the flow passage is communicably connected with the heated air generating part, and a terminal end of the flow passage constitutes a blow-off outlet for the hot vapor.

8. A thermal therapy applied to a human body, comprising:

inducing heat shock protein synthesis in tissues of the human body by elevating a temperature of a deep part of a human body by 1° C. and maintaining said elevated temperature for at least 15 minutes, said elevating and maintaining being achieved by allowing a person to inhale hot vapor such that heat is transferred to blood in capillary vessels distributed through an upper respiratory tract, a lower respiratory tract and a gas exchanging organ; and wherein said elevating and maintaining is performed at least once per day for at least two weeks.

* * * * *